United States Patent [19]

Faraj

[11] Patent Number: 5,312,995
[45] Date of Patent: May 17, 1994

[54] PROCESS FOR ISOMERIZING EPOXIDES TO ALDEHYDES

[75] Inventor: Mahmoud K. Faraj, Newtown Square, Pa.

[73] Assignee: ARCO Chemical Technology, L.P., Wilmington, Del.

[21] Appl. No.: 53,026

[22] Filed: Apr. 23, 1993

[51] Int. Cl.$^5$ .............................................. C07C 45/67
[52] U.S. Cl. ..................................... 568/427; 568/450
[58] Field of Search ........................ 568/427, 450, 426

[56] References Cited

U.S. PATENT DOCUMENTS

| | | | |
|---|---|---|---|
| 2,628,255 | 2/1953 | Sexton et al. | 260/599 |
| 2,660,609 | 11/1953 | Robeson et al | 260/601 |
| 2,694,090 | 11/1954 | Wild et al. | 260/601 |
| 4,495,371 | 1/1985 | Neri | 568/427 |
| 4,709,097 | 11/1987 | Hoelderich et al. | 568/443 |
| 4,929,765 | 5/1990 | Smuda et al. | 568/427 |
| 4,939,280 | 7/1990 | Hoelderich et al. | 549/13 |
| 4,980,511 | 12/1990 | Hoelderich et al. | 568/310 |
| 5,225,602 | 7/1993 | Hoelderich et al. | 568/427 |

OTHER PUBLICATIONS

*The Isomerization of Propylene Oxide on Zeolite Catalysts, Bulletin of the Chemical Society of Japan*, vol. 45, 3251–3254 (1972).

*Ion Exchange in Synthetic Zeolites,* Part 1–Ammonium and some its alkyl Derivatives in Linde Sieves X and Y, By B. K. G. Theng, E. Vansant and J. B. Uytterhoeven. pp. 3370–3383.

*Thermodynamics and Thermochemistry of Cation Exchange in Zeolite Y* R. W. Barrer, J. A. Davies and L. V. C. Rees, *J. inorg. nucl. Chem.*, (1986) vol. 30, pp. 3333–3349 Pergammon Press.

"Ion Exchange Reactions in Zeolite", in *Zeolite Molecular Sieves: Structure, Chemistry and Use* (1974), Donald W. Breck, Cahpter 7, pp. 529–592.

Primary Examiner—Werren B. Lone
Attorney, Agent, or Firm—Jonathan L. Schuchardt

[57] ABSTRACT

A process for isomerizing epoxides to aldehydes is disclosed. The process uses a metal-exchanged zeolite catalyst wherein the zeolite contains an alkali metal and one or more second exchangeable metals from Group IIA, IB, IIB, or IIIB. The catalysts are easily made by combining alkali metal-exchanged zeolites with aqueous solutions that contain halides or nitrates of the second metal. The process is useful for vapor-phase isomerization of propylene oxide to propanal.

15 Claims, No Drawings

PROCESS FOR ISOMERIZING EPOXIDES TO ALDEHYDES

FIELD OF THE INVENTION

The invention relates to the production of aldehydes. In particular, the invention is a process for producing aldehydes by isomerization of epoxides in the presence of certain metal-exchanged Y-zeolites.

BACKGROUND OF THE INVENTION

Lower linear aldehydes are useful direct precursors for lower primary alcohols, which are valuable solvents. Higher primary alcohols and aromatic alcohols have value as solvents, plasticizers, detergents, and fragrances. Higher primary alcohols, such as 2-ethylhexanol, are often made by aldol condensation of lower linear aldehydes, followed by hydrogenation. The aldehydes are usually made by hydroformylation of olefins. Unfortunately, hydroformylation usually gives mixtures of terminal and non-terminal aldehyde products, which limits yields of the desired linear, primary alcohols.

One way to get linear aldehydes is to isomerize epoxides. The challenge becomes finding a way to isomerize the epoxide selectively and economically. Various types of solid catalysts have been used to isomerize epoxides to aldehydes, such as magnesium silicate (U.S. Pat. No. 2,628,255), fluidized silica gel or fuller's earth (U.S. Pat. No. 2,660,609), and acidic zeolites (U.S. Pat. No. 2,694,090).

When zeolites are used, acidic zeolites are generally taught as preferred (see, e.g., U.S. Pat. No. 4,980,511). Imanaka et al. (*Bull. Chem. Soc. Jap.* 45 (1972) 3251) teach to isomerize propylene oxide to propanal using zeolite catalysts. With H-Y-zeolite, conversion to propanal was about 13%, while use of the more neutral sodium-exchanged Y-zeolite gave about 0% conversion. Platinum and palladium-exchanged Y-zeolites gave about 10% conversion. Unfortunately, these processes are not commercially attractive because of their low conversions and low aldehyde selectivities.

A desirable process would be highly selective to the aldehyde and would give good epoxide conversions. Preferably, the process would be easy to perform in the vapor phase with a continuous unit. Ideally, the process would use an easily made solid catalyst based on an inexpensive source such as alkali metal-exchanged zeolites.

SUMMARY OF THE INVENTION

The invention is a process for isomerizing an epoxide to an aldehyde. The isomerization is performed by reacting the epoxide in the presence of a metal-exchanged zeolite catalyst. The zeolite contains an alkali metal and one or more second exchangeable metals selected from the group consisting of Group IIA, Group IB, Group IIB, and Group IIIB metals. The process of the invention selectively gives high yields of terminal aldehydes.

Because it is a selective route to terminal aldehydes, the process of the invention avoids the selectivity problem inherent in the alternative hydroformylation process. Also, the process of the invention can be conveniently performed in the vapor phase, which eliminates many of the isolation, purification, and waste generation problems of alternative processes.

DETAILED DESCRIPTION OF THE INVENTION

In the process of the invention, an epoxide is isomerized to an aldehyde, preferably in the vapor phase, in the presence of a metal-exchanged zeolite catalyst.

Epoxides useful in the invention contain one or more epoxy groups, and can be prepared by epoxidizing terminal olefins. Preferred epoxides have the general structure:

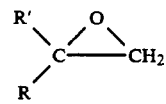

in which each of R and R' represents hydrogen or a $C_1$–$C_{30}$ alkyl, aryl, or aralkyl group. The resulting preferred aldehyde products have the general structure:

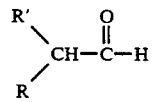

in which R and R' are as described above. Suitable epoxides include, but are not limited to, ethylene oxide, propylene oxide, 1,2-butene oxide, isobutylene oxide, diisobutylene oxide, styrene oxide, 3-phenyl-1,2-epoxypropane, and the like, and mixtures thereof. Propylene oxide is particularly preferred.

Catalysts useful in the process of the invention are metal-exchanged zeolites. The zeolites contain an alkali metal and one or more second exchangeable metals selected from the group consisting of Group IIA, Group IB, Group IIB, and Group IIIB metals. Any zeolite that can contain an exchangeable alkali metal can be used to make the catalysts useful for the process of the invention. Examples of suitable zeolites are alkali metal-exchanged Y-zeolites, X-zeolites, A-zeolites, ZSM-5, mordenites, and the like, and mixtures thereof. Alkali metal-exchanged Y-zeolites are preferred.

Although unmodified alkali metal-exchanged zeolites, such as Na-Y-zeolite, are generally unsuitable for use in the process of the invention, I have surprisingly found that at least a partial exchange of the alkali metal with a second exchangeable metal remarkably improves the suitability of the metal-exchanged zeolite for epoxide isomerization to aldehydes. The second metal is one or more metals selected from Group IIA, Group IB, Group IIB, and Group IIIB. Examples of suitable second metals include, but are not limited to, magnesium, calcium, zinc, silver, copper, and lanthanum.

The proportion of the second metal to the alkali metal in the metal-exchanged zeolite is not especially critical. If desired, most or all of the alkali metal can be replaced by the second metal. Generally, it is preferred that at least about 5 mole percent of the alkali metal be replaced by the second metal. Particularly preferred are zeolites in which the amount of the second metal is within the range of about 20 to about 80 mole percent, and more preferably within the range of about 40 to about 60 mole percent, based on the total amount of exchangeable metals present.

The catalysts useful in the process of the invention are conveniently prepared by combining an alkali metal-exchanged zeolite with an aqueous solution that contains a salt of the second metal. Mixtures of various salts of Group IIA, IB, IIB, and IIIB metals can be used if desired. Chloride and nitrate salts of the second metal are especially convenient sources of the second metal, but any other suitable metal salt can be used. The slurry is mixed for a time sufficient to effect at least a partial exchange of the alkali metal by the second metal. If desired, the catalyst can be slurried multiple times with aqueous salt solution to achieve a higher degree of alkali metal exchange.

Contact times of 1 or 2 hours may suffice; more complete exchange will be achieved if the contact time is increased to 1 or 2 days. The temperature at which the alkali metal-exchanged zeolite and the aqueous salt solution are combined is not critical. Temperatures from about 10° C. to about 100° C. are generally suitable; more preferred temperatures for the exchange are within the range of about 250° C. to about 80° C.

The modified zeolite is isolated from the aqueous salt solution by any convenient means, including filtration, and is usually washed with hot water to remove residual chloride or nitrate compounds. The catalyst is then dried under vacuum, and is calcined at a temperature within the range of about 100° C. to about 600° C., preferably from about 200° C. to about 400° C., prior to use.

Other suitable techniques for preparing catalysts useful in the process of the invention are described, for example, in D. W. Breck, *Zeolite Molecular Sieves*, Chapter 7, Wiley & Sons (1973); R. M. Barrer et al., *J. Inorg. and Nucl. Chem.* 30 (1968) 3333; and B. K. G. Theng et al., *Trans. Faraday Soc.*, 64 (1968) 3370, the teachings of which are incorporated herein by reference in their entirety.

The process of the invention is preferably performed in the vapor phase. When relatively non-volatile epoxides are used as starting materials, however, the vapor-phase process will not be practical, and a liquid phase containing the epoxide will be exposed to the solid catalyst. For volatile epoxides, the vapor-phase process is suitable and offers a number of advantages.

Typically, the epoxide is passed through a fixed bed of the catalyst, which is heated to the desired reaction temperature. The residence time of the epoxide in the catalyst bed is sufficient to achieve a desired level of epoxide conversion while maintaining good selectivity to the aldehyde product. The products are condensed, collected, and analyzed to determine epoxide conversion and aldehyde selectivity. The reaction products can be further refined by distillation or any other suitable purification method to obtain a purer aldehyde product.

Although not preferred, a solvent can be used, provided that the solvent is inert to the reaction conditions. Thus, useful solvents will not react with aldehydes under the reaction conditions chosen, and will be inert in the presence of the metal-exchanged zeolite catalyst. Useful solvents must also be easily separated by distillation or other means from the aldehyde product. Examples of suitable solvents include, but are not limited to, aliphatic and aromatic hydrocarbons, halogenated hydrocarbons, ethers, and the like, and mixtures thereof.

The reaction temperature for the isomerization is preferably within the range of about 100° C. to about 400° C. More preferred is the range from about 150° C. to about 350° C.; most preferred is the range from about 250° C. to about 325° C.

The following examples merely illustrate the invention. Those skilled in the art will recognize numerous variations that are within the spirit of the invention and scope of the claims.

Catalyst Preparation

In general, catalysts are prepared by slurrying sodium Y-zeolite with a 1M aqueous solution of a metal halide or nitrate solution at room temperature. Two 48-hour exchange periods are used, and about 40–60 mole percent of the sodium initially present is exchanged by the second metal. The process is illustrated for magnesium-exchanged Na-Y-zeolite as follows.

Sodium Y-zeolite (60 g, obtained from Strem Chemicals, Inc.), is slurried in a 1M solution of magnesium chloride for 48 h at 25° C. The product is filtered, washed with hot water (3×300 mL), and is then reslurried with fresh 1M aqueous magnesium chloride for 48 h at 25° C. The product is filtered and washed with hot water (5×500 mL) to remove residual chloride compounds. The catalyst is vacuum dried at 120° C. for 12 h, and is then calcined at 300° C. for 18 h prior to use. Elemental analysis indicates that 56 mole percent of the sodium initially present is exchanged with magnesium.

EXAMPLES 1–5

Isomerization of Propylene Oxide to Propanal

The general procedure is illustrated for the magnesium catalyst. The same procedure is used to isomerize propylene oxide using additional catalysts, and the results with all of the catalysts are listed in Table 1.

The magnesium-exchanged Na-Y-zeolite catalyst prepared in Example 1 (4.5 g) is loaded into a tubular glass reactor, which is heated to 300° C. Propylene oxide is pumped through the catalyst bed at a weight hourly space velocity (WHSV) of about 2 kg PO per kg catalyst per hour. The products are collected in a chilled receiver and are analyzed by gas chromatography. Conversion of propylene oxide is 85%. Selectivities: propanal (88%), allyl alcohol (7%), 1-propanol (1.5%). Less than 5% of the products are not precursors to the primary alcohol.

TABLE 1

Isomerization of Epoxides to Aldehydes with Metal-Exchanged Na—Y-Zeolites

| Ex. No. | Catalyst M—Na—Y-Zeolite | Mole % of Na Exchanged | Epoxide | Conversion (%) | Aldehyde Sel. (%) | Allylic Alcohol Sel. (%) | n-Alcohol Sel. (%) |
|---|---|---|---|---|---|---|---|
| 1 | Mg—Na—Y-zeolite | 56 | PO | 85 | 88 | 7.0 | 1.5 |
| 2 | Ag—Na—Y-zeolite | 90 | PO | 64 | 82 | 5.0 | 4.9 |
| 3 | Cu(II)-Na—Y-zeolite | 42 | PO | 98 | 85 | 3.5 | 3.5 |
| 4 | La—Na—Y-zeolite | 40 | PO | 97 | 81 | 8.0 | 3.0 |
| 5 | Zn—Na—Y-zeolite | 48 | PO | 45 | 75 | 8.5 | 4.5 |
| C6 | Na—Y-zeolite (control) | 0 | PO | 2 | 60 | 20 | 3.4 |

TABLE 1-continued

Isomerization of Epoxides to Aldehydes with Metal-Exchanged Na—Y-Zeolites

| Ex. No. | Catalyst M—Na—Y-Zeolite | Mole % of Na Exchanged | Epoxide | Conversion (%) | Aldehyde Sel. (%) | Allylic Alcohol Sel. (%) | n-Alcohol Sel. (%) |
|---|---|---|---|---|---|---|---|
| 7 | Mg—Na—Y-zeolite | 56 | 1,2-BO | 55 | 78 | 14 | <1 |

PO = propylene oxide; 1,2-BO = 1,2-butene oxide.
All isomerizations are performed at 300° C.; WHSV = 2.0 kg epoxide/kg catalyst/hour.

COMPARATIVE EXAMPLE 6

Isomerization of Propylene Oxide to Propanal

Sodium-exchanged Y-zeolite that has not been modified by exchange with a second metal is used as the catalyst.

The procedure of Examples 1-5 is followed with Na-Y-zeolite as the catalyst. Conversion of propylene oxide is about 2%. Selectivities: propanal (60%), allyl alcohol (20%).

This example shows that failure to incorporate the second metal into the catalyst results in poor epoxide conversion. By exchanging some of the sodium with a second metal (Examples 1-5), conversion of epoxide improves to commercially acceptable levels while maintaining high selectivity to propanal.

EXAMPLE 7

Isomerization of 1,2-Butene Oxide to Butanal

The procedure of Examples 1-5 is followed, but 1,2-butene oxide is used in place of propylene oxide. The catalyst used is magnesium-exchanged Na-Y-zeolite. Conversion of 1,2-butene oxide is 55%. Selectivities: butanal (78%), crotyl alcohol (14%), methyl ethyl ketone (6%).

The preceding examples are meant only as illustrations; the invention is defined by the following claims.

I claim:

1. A process which comprises isomerizing an epoxide having the structure:

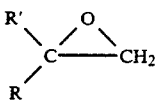

to an aldehyde having the structure:

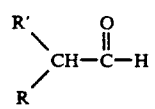

in the presence of a metal-exchanged zeolite, wherein the zeolite contains an alkali metal and a second exchangeable metal selected from the group consisting of Group IIA, Group IB, Group IIB, and Group IIIB metals; and wherein each of R and R' separately represents hydrogen, a $C_1$–$C_{30}$ alkyl group, a $C_6$–$C_{30}$ aryl group, or a $C_7$–$C_{30}$ aralkyl group.

2. The process of claim 1 wherein the epoxide is selected from the group consisting of ethylene oxide, propylene oxide, 1,2-butene oxide, isobutylene oxide, styrene oxide, and diisobutylene oxide.

3. The process of claim 1 wherein the zeolite is selected from the group consisting of Y-zeolites, X-zeolites, A-zeolites, ZSM-5, and mordenites.

4. The process of claim 1 wherein the second metal is selected from the group consisting of magnesium, silver, copper, zinc, lanthanum, and mixtures thereof.

5. The process of claim 1 wherein the process is performed in the vapor phase.

6. The process of claim 1 wherein the process is performed at a temperature within the range of about 100° C. to about 400° C.

7. The process of claim 1 wherein the amount of the second metal in the metal-exchanged zeolite is within the range of about 20 to about 80 mole percent based on the total amount of exchangeable metals present.

8. A process which comprises isomerizing an epoxide having the general structure:

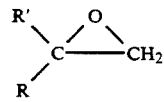

to an aldehyde having the general structure:

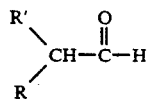

in the presence of a metal-exchanged zeolite selected from the group consisting of Y-zeolites, X-zeolites, A-zeolites, ZSM-5, and mordenites; wherein the zeolite contains an alkali metal and a second exchangeable metal selected from the group consisting of Group IIA, Group IB, Group IIB, and Group IIIB metals; and wherein each of R and R' separately represents hydrogen, a $C_1$–$C_{30}$ alkyl group, a $C_6$–$C_{30}$ aryl group, or a $C_7$–$C_{30}$ aralkyl group.

9. The process of claim 8 wherein the epoxide is selected from the group consisting of ethylene oxide, propylene oxide, 1,2-butene oxide, isobutylene oxide, styrene oxide, and diisobutylene oxide.

10. The process of claim 8 wherein the second metal is selected from the group consisting of magnesium, silver, copper, zinc, lanthanum, and mixtures thereof.

11. The process of claim 8 wherein the process is performed in the vapor phase.

12. The process of claim 8 wherein the process is performed at a temperature within the range of about 100° C. to about 400° C.

13. A process which comprises isomerizing propylene oxide to propanal in the vapor phase in the presence of a metal-exchanged Y-zeolite, wherein the Y-zeolite contains an alkali metal and a second metal selected from the group consisting of Group IIA, Group IB, Group IIB, and Group IIIB metals.

14. The process of claim 13 wherein the second metal is selected from the group consisting of magnesium, silver, copper, zinc, lanthanum, and mixtures thereof.

15. The process of claim wherein the process is performed at a temperature within the range of about 100° C. to about 400° C.

* * * * *